United States Patent
Bounaix

(10) Patent No.: US 7,352,463 B2
(45) Date of Patent: Apr. 1, 2008

(54) METHOD AND DEVICE FOR DETECTING GASES BY ABSORPTION SPECTROSCOPY

(75) Inventor: Fabrice Marcel S. Bounaix, Hoerdt (FR)

(73) Assignee: TDW Delaware, Inc., Wilmington, DE (US)

( * ) Notice: Subject to any disclaimer, the term of this patent is extended or adjusted under 35 U.S.C. 154(b) by 416 days.

(21) Appl. No.: 10/525,850

(22) PCT Filed: Sep. 6, 2002

(86) PCT No.: PCT/US02/28377

§ 371 (c)(1),
(2), (4) Date: Feb. 25, 2005

(87) PCT Pub. No.: WO2004/023114

PCT Pub. Date: Mar. 18, 2004

(65) Prior Publication Data

US 2006/0119851 A1    Jun. 8, 2006

(51) Int. Cl.
*G01N 21/00* (2006.01)

(52) U.S. Cl. .................................... 356/437
(58) Field of Classification Search ................ 356/437
See application file for complete search history.

(56) References Cited

U.S. PATENT DOCUMENTS 5,705,816 A   1/1998   Ronge et al.
2003/0072009 A1*   4/2003   Domash et al. ............. 356/519
2005/0134859 A1*   6/2005   Kalayeh et al. ............. 356/437

FOREIGN PATENT DOCUMENTS

EP        1070943 A1    1/2001
GB        2286458 A     4/1994
WO   PCT US02/28377    3/2004

* cited by examiner

*Primary Examiner*—Gregory J. Toatley, Jr.
*Assistant Examiner*—Amanda H Merlino
(74) *Attorney, Agent, or Firm*—Gable Gotwals

(57) ABSTRACT

A method and device for measuring a concentration of a preselected gas in a gas sample are disclosed. The device comprises a Herriott type multipass cell (10) having a center axle (74) and a housing (80A, 80B) surrounding and spaced from the axle to provide a tubular sample cavity (84). The gas sample is pumped through the sample cavity via apertures (154, 156) provided in opposed ends of the axle. A first mirror (44) and a second mirror (46) are supported at opposed ends of the axle. A light source, e.g. a laser or LED, is provided for emitting a light beam into the sample cavity via an entry aperture (30) in the first mirror, the light beam having a wave length at which the preselected gas strongly absorbs. The beam is reflected between the mirrors for a number of times before exiting the cell via an exit aperture (48) in the second mirror and impinging on a detector (52). The device further comprises a reference detector (32) for monitoring the intensity of the unattenuated light beam and a detector for detecting the intensity of light transmitted through the second mirror after a single pass through the cell. The light source is operatively connected to a heat control assembly having a heat sink and the gas sample is passed said heat sink to augment temperature control of the light source.

22 Claims, 9 Drawing Sheets

METHOD AND DEVICE FOR DETECTING GASES BY ABSORPTION SPECTROSCOPY

BACKGROUND OF THE INVENTION

A common means of distributing energy around the world is by the transmission of gas, usually natural gas, but in some areas of the world manufactured gasses are also transmitted for use in homes and factories. Gas is typically transmitted through underground pipelines having branches that extend into homes and other buildings for use in providing energy for space and water heating. Many thousands of miles of gas pipeline exists in virtually every major city of the world. Since gas is useable only because it is highly combustible, gas leakage is a serious concern. For this reason much effort has been made to provide instrumentation for detecting small amounts of gas so that leaks can be located to permit repairs.

A known and successful system for detecting small quantities of gas in the environment is by the use of absorption spectroscopy. By this technique, a light beam of a selected frequency that is highly absorbed by the particular gas for which the instrument is designed is passed through a sample of the gas. The rate of absorption of the light beam is used as an indicator of the level of concentration of the gas in the sample. A basic element of natural gas, and most manufactured gasses used for room and water heating around the world, is methane. By initiating a beam of light at a frequency that is highly absorbed by methane and passing the beam through a sample of gas the level of concentration of methane in the gas sample can be determined.

In order to improve the sensitivity of detecting low levels of concentration of gas by spectral absorption, it is necessary to pass the light beam through a relatively long pathway of gas sample. Stating it another way, as the length of the light beam passing through a sample is increased, the sensitivity of the instrument to detect very small levels of gasses increase.

It is easy to understand that if a beam is passed through a very long tube containing a sample of gas that the instruments requiring such a long tube would be extremely cumbersome and therefore not easily portable. To overcome this problem, others have devised systems wherein a beam of light is repeatedly reflected between opposed mirrors to thereby extend the length of exposure of the beam to a gas sample in a way that the size of the instrument can be substantially reduced. A typical absorption cell is an elongated cylinder in which mirrors are disposed at opposite ends and light is introduced into the cells through a hole in one of the mirrors. For background information relating to the use of optical devices that provide for multiple traverses of light within a test cell having opposed mirrors reference can be had to the article entitled "Long Optical Paths of Large Aperture" by J. White *J. Opt. Soc. Am.* Vol 32, p. 285-288, May 1942. Another example of background information on this subject is entitled "Off-Axis Paths in Spherical Mirror Interferometers" by Herriott et al. in Applied Optics Vol. 3 pages 523-526. A further article by Herriott et al. entitled "Folded Optical Delay Lines" is found in *Applied Optics*, Vol 4 p. 883-889, August 1965. Because of the early work by Herriott in the development of light absorption spectroscopy using a cell having opposed mirrors in which a light beam is repeatedly reflected, such instruments are frequently referred to as "Herriott cells." The invention herein relates to improvements and innovations in the construction, operation and use of Herriott type cells for detecting a selected gas, such as methane. Particularly, the invention herein provides methods and systems for detecting and measuring the level of concentration of a preselected gas using an instrument that is more portable, rugged and sensitive than other instruments and systems currently available.

For further background information relating to the basic subject matter of the invention herein reference maybe had to the following previously issued United States patents and other publications:

| Patent or Reference No. | Inventor | Title |
| --- | --- | --- |
| 3,253,226 | Herriott et al. | Optical Maser Amplifier |
| 3,437,954 | Herriott et al. | Optical Delay Line Devices |
| 3,550,039 | Herriott et al. | Optical Delay System |
| 4,934,816 | Silver et al. | Laser Absorption Detection Enhancing Apparatus and Method |
| 5,002,351 | Wolfum et al. | Fusion Splicer for Optical Fibers |
| 5,121,405 | Negus | Alignment Control System for Lasers |
| 5,291,265 | Kebarbian | Off-axis Cavity Absorption Cell |
| 5,528,040 | Lehmann | Ring-down Cavity Spectroscopy Cell Using Continuous Wave Excitation for Trace Species Detection |
| 5,550,636 | Hagans et al. | Self-tuning Method for Monitoring the Density of a Gas Vapor Component Using a Tunable Laser |
| 5,637,872 | Tulip | Gas Detector |
| 5,946,095 | Henningsen et al. | Natural Gas Detection Apparatus and Method Operable in a Moving Vehicle |
| 5,949,537 | Inman et al. | In-line Cell for Absorption Spectroscopy |
| 6,064,488 | Brand et al. | Method and Apparatus for In Situ Gas Concentration Measurement |
| 6,157,033 | Chudnovsky | Leak Detection System |
| US PUB 2002/0011568 | Diekmann | Infrared Optical Gas Sensor |
| US PUB 2002/0015427 | Pilgrim et al. | Wavelength Agile External Cavity Diode Laser |
| US PUB 2002/0018496 | Gutin | Tunable Diode Laser System, Apparatus and Method |
| US PUB 2002/0040590 | Schley | Method and Device for Determining the Gas Properties of a Combustible Gas |
| US PUB 2001/0045119 | Warburton | Method and Apparatus for Determining Concentration of a Gas |
| FR PUB | Ronge et al. | Precede et Dispositif de Trace d'Impuretes dans un Echantillon de gaz au Moyen d'une Diode Laser a Semiconducteur |
| FR PUB H3-260859 | Takeuchi et al. | Water Content Analysis Device Using Semiconductor Laser, Double Wavelength Differential Absorption Method |
| FR PUB H5-99845 | Takeuchi et al. | Analyseur de Teneur en eau Utilisant un Laser a Semiconducteur |

Other Publications:

"Folded Optical Delay Lines," Herriott et al., *Applied Optics* August 1965.

"Laser Beams and Resonators," Kogelnik et al., *Applied Optics* October 1966.

"Narrow Optical Interference Fringes for Certain Setup Conditions in Multipass Absorption Cells of the Herriott Type," McManus et al., *Applied Optics* Mar. 1, 1990.

"Measurement of Water Vapor Pressure and Activity Using Infrared Diode Laser Absorption Spectroscopy", S. A. Bone, P. G. Cummins, P. B. Davies, S. A. Johnson, *Applied Spectroscopy*, Vol 47, no 6, 1993.

"Diode-Laser Absorption Technique for Simultaneous Measurements of Multiple Gas Dynamic Parameters in High-speed Flows Containing Water Vapor", M. P. Arroyo, S. Langlois, R. K. Hanson; *Applied Optics*, Vol 33, no 15, 1994.

"Diode Laser Measurements of $H_2O$ Line Intensities And Self-Broadening Coefficients in the 1,4-μm Region", S. Langlois, T. P. Birbeck and R. K. Hanson; *Journal of Molecular Spectroscopy*, Vol 163, p 27-42, 1994.

"Absorption Measurements of Water Vapor Concentration, Temperature, and Line-shape Parameters Using a Tunable InGaAsP Diode Laser", M. P. Arroyo and R. K. Hanson; *Applied Optics*, Vol 32, no 30, 1993.

"Infrared Diode Laser Determination of Trace Moisture in Gasses", J. A. Mucha, L. C. Barbalas, *ISA Transactions*, Vol 25, no 3, 1986.

"Application of Tunable Diode Lasers in Control of High Pure Material Technologies", G. G. Devyatykh[h], V. A. Khorshev[h], G. A. Maksimov[h], A. I. Nadezhdinskii[A], S. M. Shapin[h], Preprint.

"Laser Absorption IR Spectrometer for Molecular Analysis of High Purity Volatile Substances. Detection of Trace Water Concentrations in Oxygen Argon and Monogermane", G. G. Devyatykh, G. A. Maksimov, A. I. Nadezhdinskii, V. A. Khorshev, S. H. Shapin; *SPIE* Vol 1724 "Turnable Diode Laser Applications".

"Application of FM Spectroscopy in Atmospheric Trace Gas Monitoring: A Study of Some Factors Influencing the Instrument Design", P. Werle, K. Josek and F. Slemr, *SPIE* Vol 1433 "Measurement Of Atmospheric Gases", 1991.

"Stable Isotope Analysis using Tunable Diode Laser Spectroscopy", Joseph F. Becker, Todd B. Sauke and Max. Loewenstein, *Applied Optics*, Vol 31, no 12, 1992.

"High Sensitivity Detection of Trace Gases using Sweep Integration and Tunable Diode Lasers", D. T. Cassidy and J. Reid, *Applied Optics*, Vol 21, no 14, 1982.

"Atmospheric Pressure Monitoring of Trace Gases using Tunable Diode Lasers", D. T. Cassidy and J. Reid, *Applied Optics*, Vol 21, no 7, 1982.

"Near Infrared Diode Lasers Measure Greenhouse Gases", A. Stanton, C. Hovde, *Laser Focus World*, August 1992.

"Airborne Measurements of Humidity Using A Single Mode Pb Salt Diode Laser", Joel A. Silver and Alan C. Stanton, *Applied Optics*, Vol 26, no 13, 1987.

"Diode Laser Spectroscopy for On Line Chemical Analysis"; David S. Bomse, David C. Hovde, Daniel B. Oh, Joel A. Silver and Alan C. Stanton, *SPIE* Vol 1681, "Optically Based Method for Process Analysis", 1992.

"Two-mirror Multipass Absorption Cell", J. Altmann, R. Baumgart and C. Weitkamp; *Applied Optics*, Vol 20, no 6, 1981.

"Long Optical Paths of Large Aperture", J. White; *J. Opt. Soc. Am*. Vol 32, p 285-288, May 1942.

"Folded Optical Delay Lines", Herriott et al.; *Applied Optics*, Vol 4 p 883-889, August 1965.

"Off Axis Paths in Spherical Mirror Interferometers", D. Herriott, H. Kogelnik, R. Komper; *Applied Optics*, Vol 3 no 4, 1964.

BRIEF SUMMARY OF THE INVENTION

A method of detecting a preselected gas, such as methane, includes the steps of continuously moving a stream of sample gas through a confined testing area within a detecting instrument. A light source, such as a laser emitting diode or a light emitting diode is energized within the test instrument to emit a beam of frequency that is highly absorbed by the preselected gas. The beam is passed through the stream of gas within the confined testing area by bouncing the beam repeatedly between spaced apart mirrors in a Herriott type cell so that the length of travel of the beam within the test gas is greatly extended. Absorption of the beam is measured to provide an indication of the presence of the preselected gas.

The frequency of light emitted by a typical light source, such as a laser diode or light emitting diode, is affected by the temperature of the light source and therefore the temperature must be regulated. By the provision of the invention disclosed herein, the sample gas stream, after having passed through the testing area is conducted past a heat control assembly.

The heat control assembly includes a heat sink having cooling fins that are exposed to the stream of sample gas, the light source being mounted in contact with a peltier element that in turn is in heat conductive relationship with the heat sink. A thermistor senses the temperature of the heat sink and sends a control signal to a microprocessor that in turn sends temperature adjustment instructions to a power supply which then provides adjusted current to the peltier that adjusts the temperature of the light source.

The Herriott type cell as used in the gas detection instrument of this invention is significantly improved by the incorporation of a central axle member that provides a confined annular shaped test area for the sample gas through which the light beam moves.

A system is provided employing three photo detectors—that is: (a) a reference photo detector; (b) a multi-path photo detector; and (c) a single or direct path photo detector. By employing measurements of the three reference photo detectors the concentration of gas in the test sample can be determined with accuracy over a wider range than is typically available with existing instrumentation.

The Herriott type absorption spectroscopy cell as used herein is improved in important ways including the provision wherein a light beam enters through an aperture in a first mirror and exists, after multiple passes, through an aperture in a second mirror to encounter a multi-pass photo detector. Simultaneously provision is made for measuring absorption after a single pass of the light beam. Activation of the reference photo detector is achieved by a beam splitter window.

The invention herein provides a highly portable yet rugged system that it easily adaptable to mounting in a vehicle so that test samples can be continuously picked up from the environment and cycled through the test system while the vehicle is moving to enable an operator to expeditiously survey a relatively large geographical area. This highly portable system used in a vehicle provides readouts coordinated with a global positioning monitor so that gas level intensities of a geographical area can be quickly and accurately mapped.

A better understanding of the invention will be obtained from the following detailed description and claims, taken in conjunction with the attached drawings.

BRIEF DESCRIPTION OF THE DRAWINGS

FIG. 5 shows the intermediate portion of the cell in cross section to reveal the annular gas sample passageway.

DETAILED DESCRIPTION OF THE PREFERRED EMBODIMENTS

Figure 1:
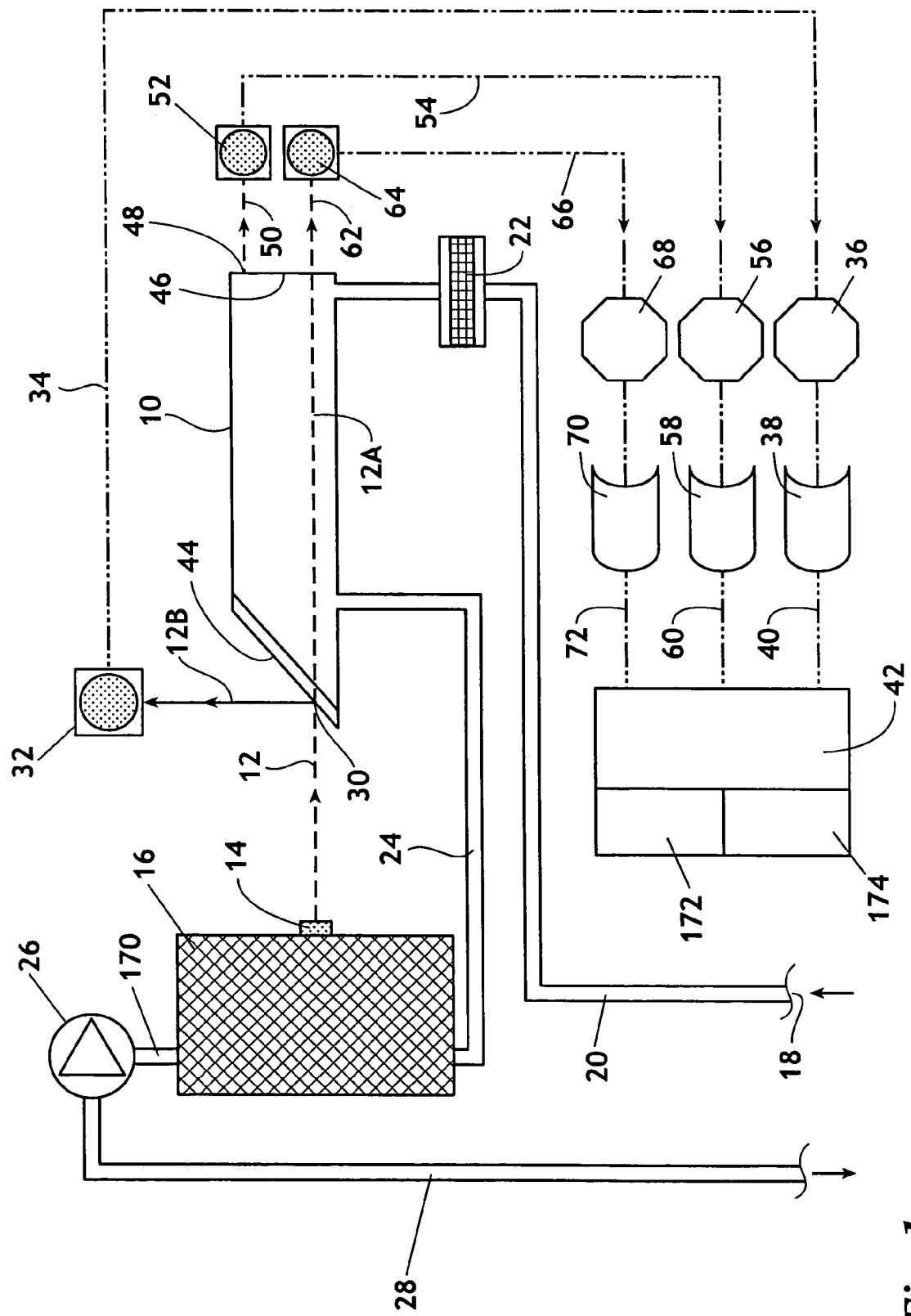
FIG. 1 is a diagrammatic representation of the basic elements making up the system of this invention for providing gas detection by light absorption spectroscopy. The system of this invention can be used for detecting extremely low-level concentrations of a selected gas, such as methane. The system is characterized by its portability and ruggedness. It can be either hand carried into a closed or confined environments or utilized in a moving vehicle by which maps can be generated showing the gas concentration levels of geographical areas.

Referring to the drawings and first FIG. 1, a block diagram of the major components of a system that can be used in practicing the methods of this invention are illustrated. The heart of the system is a cell 10 that will be described in detail subsequently, and that provides an environment in which a light beam 12 passes through a gas sample and in which absorption of the light beam is measured.

The invention will be described in which a light beam is provided by a laser diode, in which case light beam 12 is a laser light beam. However, the invention can be practiced using a light source that provides a non-coherent light beam. An example of a non-coherent light source is a light emitting diode (LED). A laser diode provides a coherent light beam that is a beam of substantially uniform frequency light having the characteristic that the laser light beam does not disperse to the same extent as a non-coherent light beam. The use of a laser beam, such as produced by a laser diode, is advantageous, but the use of a laser diode is not indispensable. However, laser diodes are expensive compared to LEDs. In some applications, LEDs work satisfactorily. As used throughout this description, "laser beam" or "laser diode" are inclusive of "light beam" or "LED."

Supported to cell 10 is a structure that includes a laser diode 14 that, when energized, produces laser beam 12. Laser diodes of the type represented by 14 are temperature sensitive. That is, the frequency of the laser light produced by diode 14 varies according to the temperature of the diode. For measurement accuracy it is important that the frequency of laser beam 12 be controlled within a fairly narrow range, which in turn means that the temperature of laser diode 14 must be controlled. For this purpose, a temperature regulating system generally indicated by the block 16 is employed and will be described in detail subsequently.

The invention herein functions by moving laser beam 12 through a gas sample and determining the level of concentration of a selected gas in the gas sample by measuring absorption of the laser beam. This technology is generally referred to as "laser absorption spectroscopy." Cell 10, including the components secured in relation to it, provide a tunable laser diode absorption spectroscope. Flow channels are provided by which a gas sample is moved through cell 10. Sample gas is taken in through an inlet 18 in inlet tube 20 and flows through filter 22 into the interior of cell 10. The gas flows through cell 10 to an outlet tube 24 that connects with temperature regulating system 16. Gas is moved through the system by means of a gas pump 26 to a discharge tube 28 by which the gas sample is returned to the environment.

Laser beam 12 passes through a window (to be described subsequently). A portion of the beam passes through an aperture 30 in a first mirror 44. The number 12A represents the first pass of the beam internally of cell 10. A portion of laser beam 12 is reflected by the window, the reflected beam being indicated by the numeral 12B. A photo detector 32 is placed to receive the interception of reflected beam 12B and provides an electrical signal that is representative of the intensity of laser beam 12. The electrical signal from photo detector 32 is conveyed by conductor 34 to an amplifier 36 that feeds into a analog to digital converter circuit 38 that provides a referenced digital input over conductor 40 that feeds into a microprocessor 42.

Cell 10 is of a type generally known as a "Herriott" cell. This name is derived from the inventor of a cell that employs opposed mirrors that reflect a light beam back and forth between them so that a relatively long path can be obtained in a relatively shorter length instrument, and in which the path is in a circular pattern. While generally of the "Herriott" type, cell 10 of this invention has many improvements and innovations as will be described subsequently in detail.

Cell 10 employs a first mirror 44 and an opposed second mirror 46. A small aperture 30 is provided in first mirror 44 through which the laser beam passes and forms beam 12A within the cell that first impacts second mirror 46. Beam 12A is reflected sequentially between mirrors 44 and 46 a number of times before exiting second mirror 46 through a small aperture 48. The exit beam 50 impinges on a second photo detector 52 that provides a signal on conductor 54 feeding an amplifier circuit 56 that feeds a second analog to digital converter 58 that provides a digital signal on conductor 60 leading to microprocessor 42.

The methods, and the systems for practicing the methods, of this invention are used to detect selected gasses such as methane, butane, propane, ethane, oxygen, hydrogen, nitrogen, $H_2O$, hydrogen fluoride, hydrogen chloride, hydrogen boride, hydrogen sulfide, ammonia, CO, $CO_2$, NO, $NO_2$ and $SF_6$. The system can be adapted to detect different selected gases by changing out the laser diode to one that produces the frequency of light most readily absorbed by the gas of interest. When a light emitting diode (rather than a laser diode) is used, the broader spectrum of light produced by it can detect more different gases but usually at higher concentrations. The system will be described as it is particularly useful in detecting methane gas since methane is the basic component of natural gas and most manufactured fuel gasses. If a leak occurs in a gas distribution system it can usually be located by detecting the presence of methane. Therefore, cell 10 employs a laser diode 14 that produces a beam characterized by a frequency that corresponds to a high degree of absorption by methane. Sample gas that is drawn in through inlet 18 and flows by way of inlet tube 20 into and through cell 10 absorbs, that is, decreases the intensity of light beam 12A in proportion to the quantity of methane contained in the sample gas.

Light beam 50 passes out aperture 48 in second mirror 46 after having been reflected many times between mirrors 44 and 46. The way this is achieved will be described subsequently. Undergoing multiple reflections from the time beam 12A enters cell 10 until it exits through aperture 48 means that the beam has traversed a relatively long path equal to many times the length of cell 10 which in turn means that ample provision has been made for absorption of the light beam by the presence of methane in the gas sampler.

By comparing the intensity of the signal on conductor 34 with that on conductor 54 the concentration of methane in the sample gas passing through cell 10 can be ascertained. By accurate processing within microprocessor 42 the amount of methane contained in the sample gas passing through cell 10 can be determined with great accuracy and can be expressed such as in parts per million. The presence of methane can be detected at a sensitivity down to a few parts per million or even, ideally, to a sensitivity of one or less than one part per million.

As previously stated, beam 12 emanating from laser 14 passes through a first aperture 30 in first mirror 44 to provide beam 12A within the cell. When the initial passage of laser beam 12A within cell 10 encounters second mirror 46 most of the beam intensity is reflected back towards first mirror 44 and subsequently repeatedly reflected between first mirror 44 and second mirror 46 to finally pass out through second window 48 to form exit beam 50. However, when beam 12A strikes second mirror 46 a small portion of the intensity of the beam passes through the mirror even though no aperture or window is provided since most mirrored surfaces are not 100% reflective. The portion of light beam 12A that passes through second mirror 46 provides a second exit beam 62 that engages a third photo detector 64. This produces an electrical signal on conductor 66 passing to a third amplifier 68 that feeds an analog to digital converter 70 sending a digital signal by way of conductor 72 to microprocessor 42. The employment of two separate exit beams 50 and 62 emanating from cell 10 to activate photo detectors 52 and 64 is an important attribute of the invention herein. It is apparent that only signals appearing on conductors 40 and 60 feeding microprocessor 42 are required to measure low levels of concentration of methane in the gas passing through cell 10. It is important to detect very small levels of methane in the sample gas, which is accomplished by employing a long light path for the laser beam before the beam exits through window 48, however, this arrangement fails if a broader scale of methane detection is required. If methane is present at a relatively high level in the sample gas passing through the cell the laser beam will be substantially completely absorbed before it exists through window 48 so that insufficient intensity of the beam remains for use in computing the percentage of methane of greater concentration in the gas sample. This problem is overcome by the use of third photo detector 64. Second exit beam 62 travels a relatively short distance through the gas sample, therefore the attenuation of beam 62 occurs at a rate that can provide a measurement even when the percentage of methane in the test gas is many times that which is detectable by photo detector 52. In other words, the employment of two separate exit beams 50 and 62, one having a short length light path in the test gas and the other having a long length light path provides a system wherein the range of concentration of methane that can be measured is greatly expanded.

In the preferred practice of the invention, laser light beam 12 is not energized by a steady state voltage to produce a steady state beam but, in the contrary, laser 14 is pulsed with a saw tooth wave shaped current. Each pulsation of laser diode 14 generates a pulsed laser beam 12 that varies in frequency over a selected bandwidth. Each current pulse produces light that varies in frequency above and below the frequency that undergoes the greatest absorption of the specific gas the instrument is designed to detect.

Since laser 14 is energized by a particular pulsed current waveform, the resultant signals generated by photo detectors 32, 52 and 64 (see FIG. 1) are characterized by that particular waveform. Therefore, within microprocessor 42 absorption is detected by electronically dividing the signal of photo detectors 52 and 64 by the signal of photo detector 32.

FIGS. 2 through 7 illustrate details of a preferred embodiment of cell 10. As previously stated cell 10 is, generally speaking, of the Herriott type, however with significant and important changes, innovations, and improvements.

Figure 2:
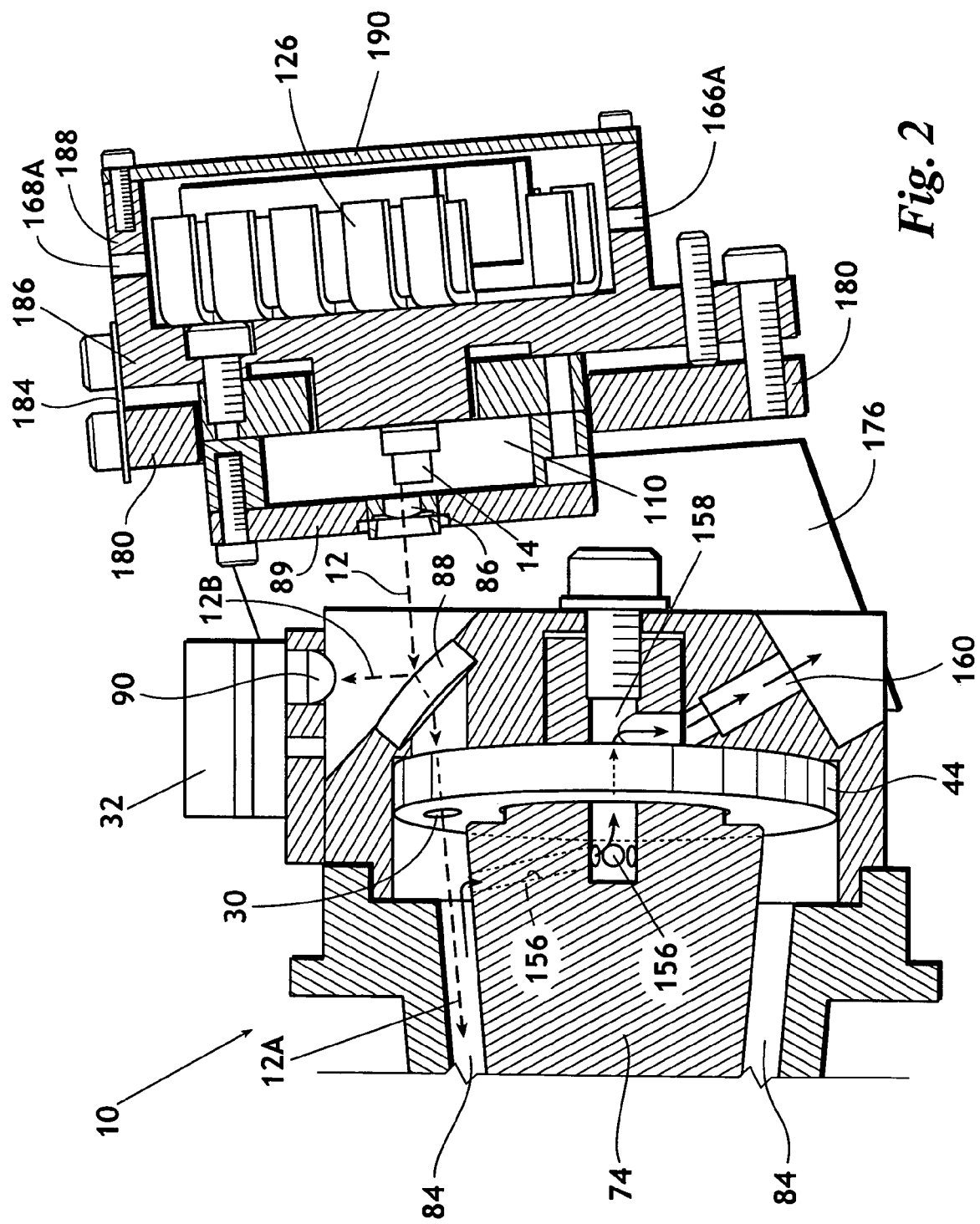
FIG. 2 is a partial elevational cross sectional view of the forward end portion of a Herriott type gas detection cell having improvements according to this invention. A light beam alignment system that uses hinge plates is illustrated in this figure.
Figure 3:
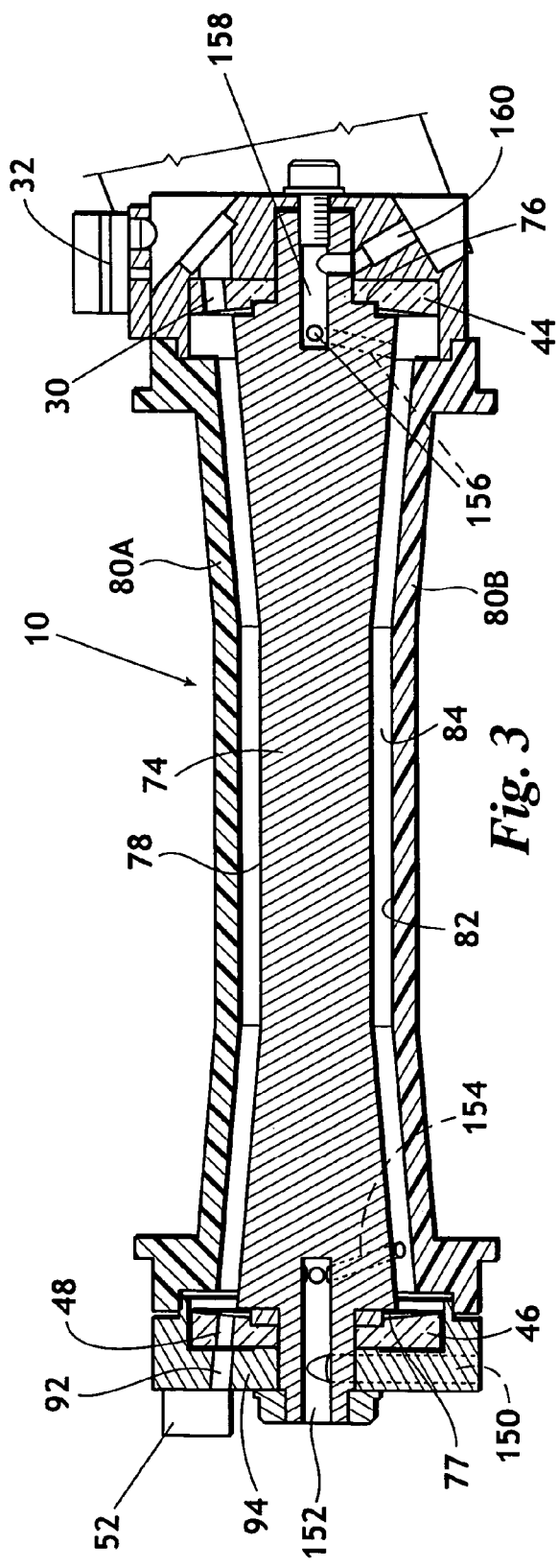
FIG. 3 is an elevational cross sectional view of an improved Herriott type cell for use in detecting gas concentration by light absorption spectroscopy showing improvements provided by this invention.

FIG. 3 is a cross-sectional view showing the basic construction of cell 10. This figure shows a structure providing first mirror 44 and second mirror 46. A unique feature of cell 10 as seen in FIGS. 2, 3, 5 and 6 is the employment of a central axle member 74 having a first end 76 that engages first mirror 44 and a second end 77 that engages second mirror 46. The exterior surface 78 of central axle 74 is contoured, that is— of less diameter in the middle than at the ends 76 and 77 for purposes, which will be described subsequently.

Figure 4:
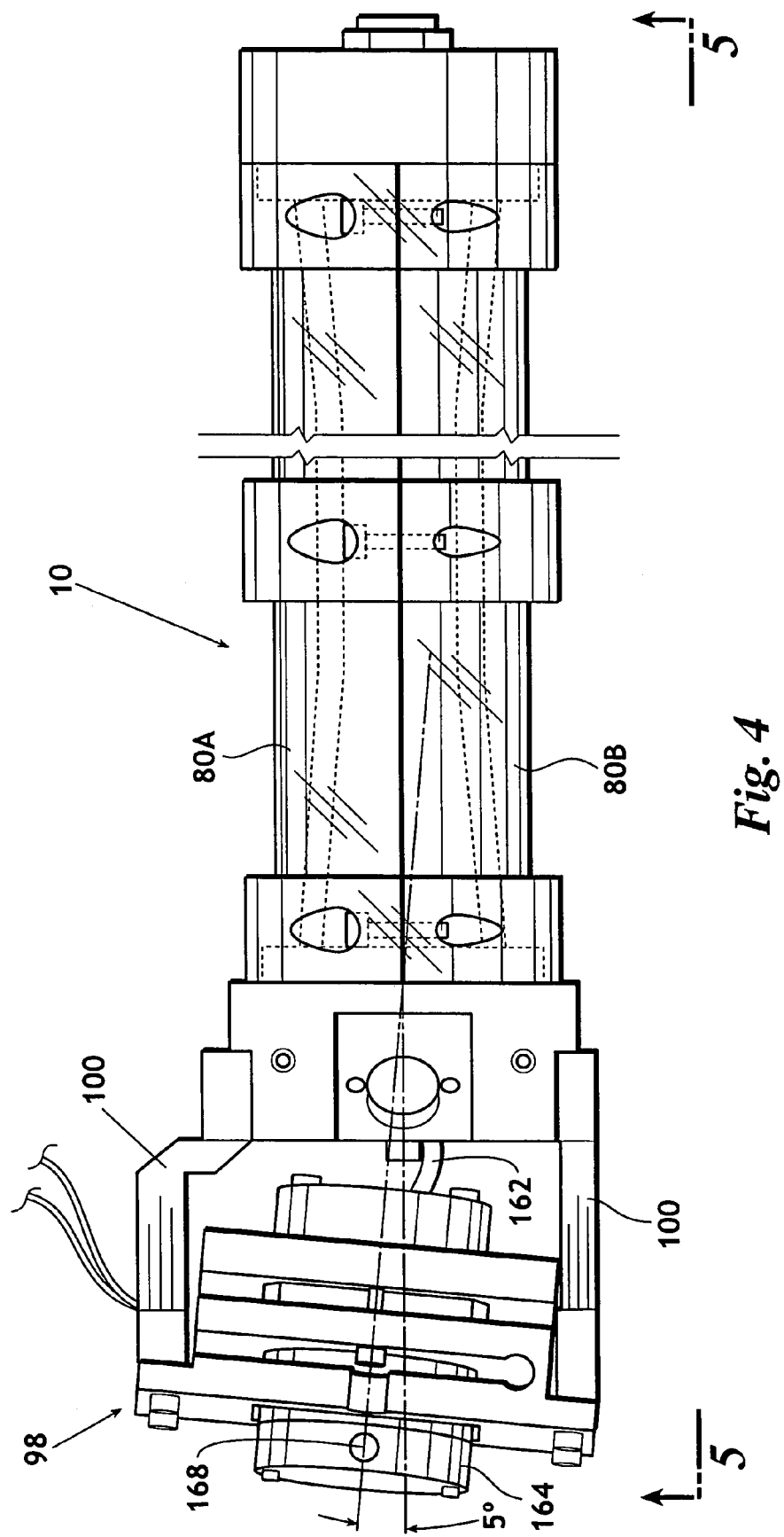
FIG. 4 is an elevational side view of the gas detecting cell employed in this invention and shows the external appearance of the cell with cover component in place that provides an annular shaped gas cavity within the cell though which sample gas flows.

Surrounding central axle 74 is a housing 80 that, in the illustrated arrangement, as shown in FIG. 4, is formed of two matching portions 80A and 80B that fit together. Housing 80A, 80B provides an interior surface 82 spaced from the central axle external surface 78 providing an elongated annular area 84. It is this annular area 84 through which sample gas moves that absorption of light from the laser diode takes place and by which the concentration of methane in the gas sample is detected.

There is formed in first mirror 44 a first aperture 30 as seen in FIG. 2. Light beam 12 from laser diode 14 first passes through a lens 86 mounted in an opening in a lens support plate 89 and encounters an inclined window 88. At window 88 a portion of beam 12 is reflected to provide the laser beam 12B that was discussed with reference to FIG. 1. Beam 12B passing through a lens 90 and encounters first photo detector 32. Beam 12 passes through inclined window 88 and through first aperture 30 in first mirror 44.

As seen in the left hand end of FIG. 3 second mirror 46 has aperture 48 as previously mentioned that is in alignment with a passageway 92 in a cap member 94 by which the beam exits from the cell. In alignment with passageway 92 is photo detector 52 described with respect to FIG. 1. In FIG. 3 aperture 30 in first mirror 44 and apertures 48 in second mirror 46 are shown as if they are in a vertical plane taken through a longitudinal axis (not shown) of axle 76. This is for purposes of illustration only as there is no requirement that they be in the same plane and as seen in FIG. 9, which will now be discussed, apertures 30 and 48 are typically not in the same plane.

Figure 9:
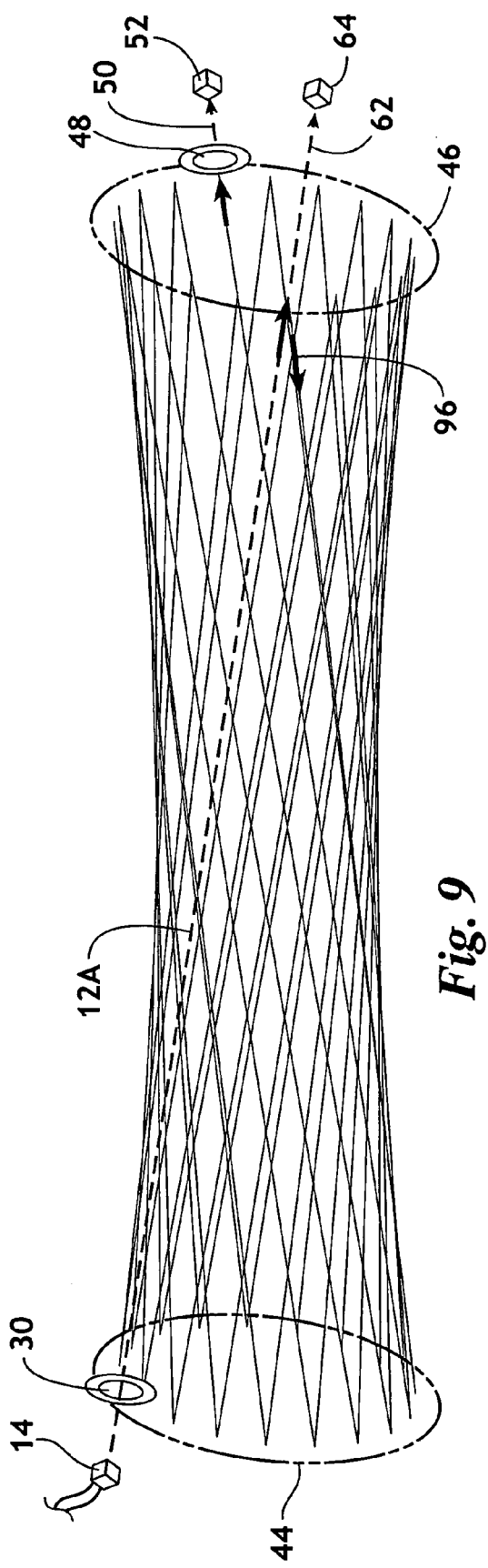
FIG. 9 is a diagrammatic illustration of the path the light beam takes within the annular cavity within the cell as the beam is reflected repeatedly from opposed mirrors to travel back and forth within the annular shaped sample gas cavity affording means for accurate measurement of absorption of the beam by the sample gas within the cell.

The pattern of light travel of the beam-entering cell 10 is illustrated in FIG. 9 wherein the first mirror 44 and second mirror 46 are represented by circles with smaller circles indicating first aperture 30 and second aperture 48. Laser diode indicated at 14 produces laser beam 12A as previously described that passes through first aperture 30 into the cell. Beam 12A strikes second mirror 46. As previously stated, a portion of beam 12A passes through second mirror 46 producing beam 62 that strikes third photo detector 64. The major portion of beam 12A is reflected as indicated by arrow 96. The beam travels back and forth between mirrors 44 and 46 a large number of times and finally exits through aperture 48 in second mirror 46, the exiting beam being indicated by numeral 50 described with respect to FIG. 1. Beam 50 strikes second photo detector 52.

FIG. 9 graphically illustrates the unique beam path that travels a plurality of times back and fourth between mirrors 44 and 46 within the annular area that surrounds the central axle. This arrangement provides a very rigid cell structure having an extremely long path through which the laser beam travels through the annular area that is continuously supplied with sample gas. This long path, achieved by multiple reflections of the light beam, provides for a high level of sensitivity of absorption of the laser beam while at the same time affords a compact, sturdy and easily portable system for detecting the presence of a selected gas, such as a methane.

As seen in FIG. 9, light beam 12A enters the cell at an oblique angle relative to the imaginary longitudinal axis of axle 74. This causes the point of incidence of the light beam striking opposed mirrors 44 and 46 to progress radially around the mirrors. The cross-sectional area of the annular absorption area 84 through which the light beam traverses between opposed mirrors 44 and 46 is greatest at the mirror surfaces and least at the midpoint between the mirrors. For this reason the diameter of axle 74 is least at the midpoint between the axle opposed ends 76 and 77 as shown in FIG. 3.

Figure 7:
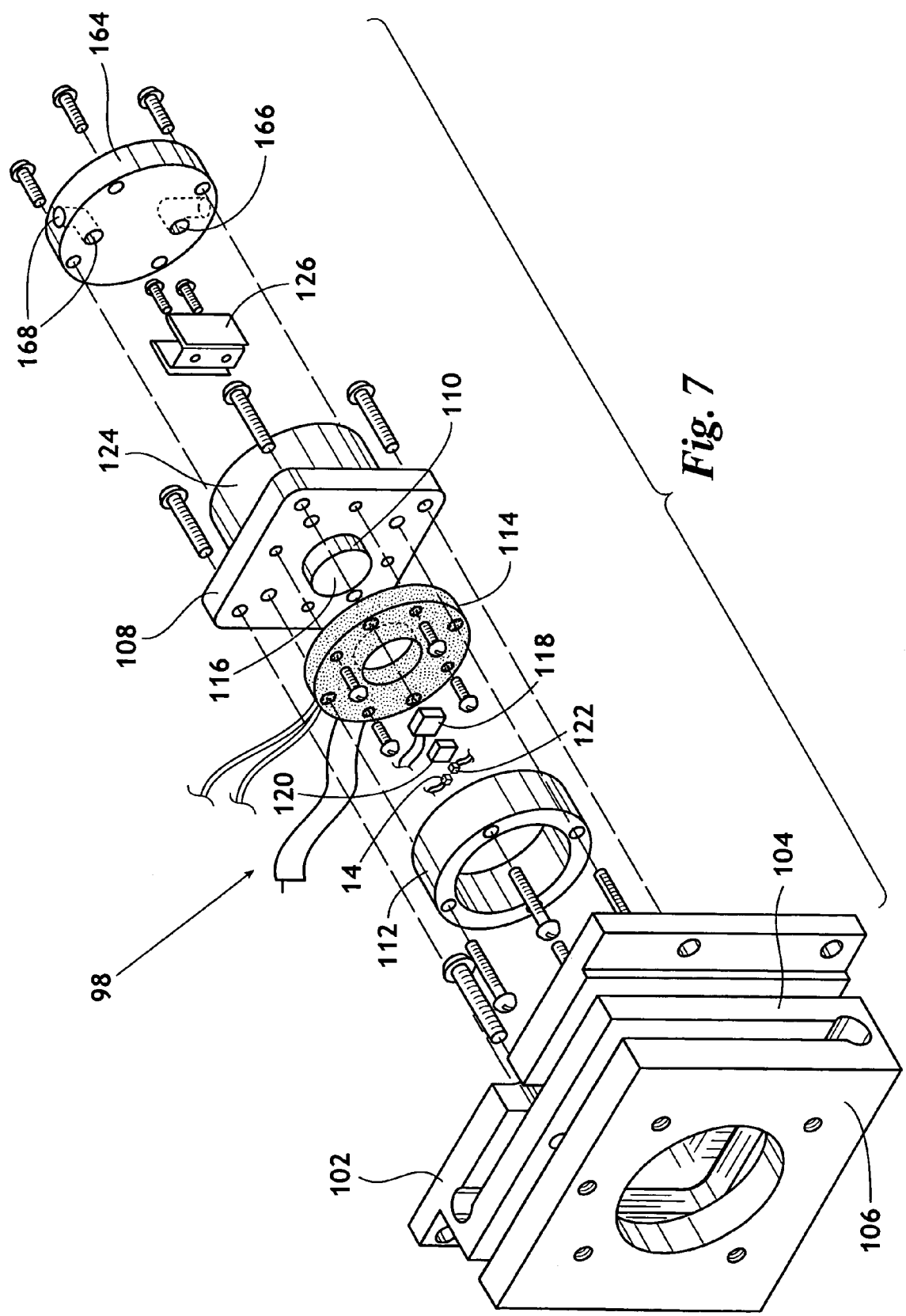
FIG. 7 is an exploded view of the forward portion of the cell that houses the light source such as a laser diode and illustrates the support structure that provides for alignment of the beam for entry into the sample gas cavity.
Figure 11:
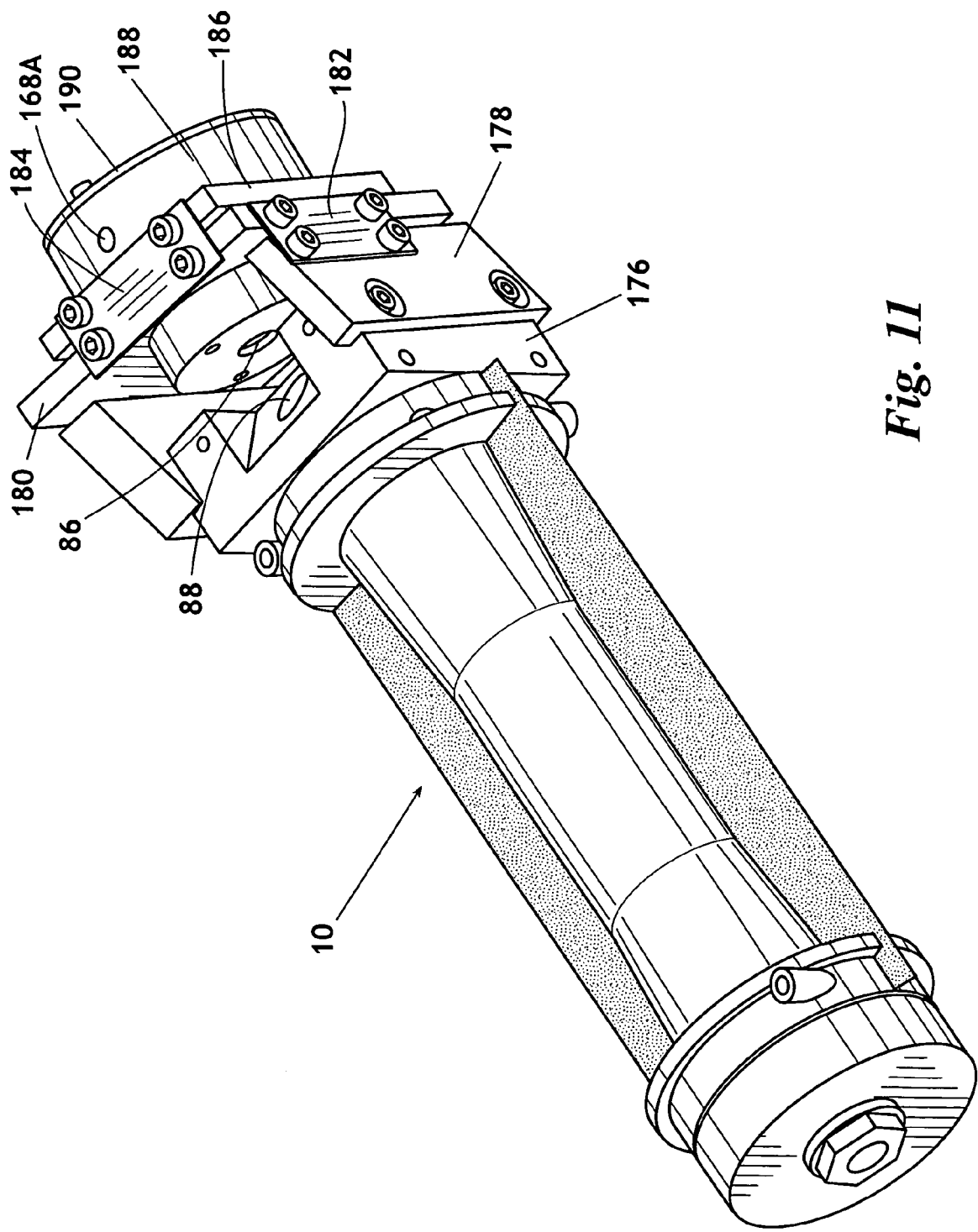
FIG. 11 is an isometric external view of a gas detection cell having a light beam alignment system that employs hinge plates.

Laser diode 14 is supported by a laser mount structure generally indicated by the numeral 98 as seen in FIGS. 4, 5, 6 and 7. A different laser mount structure 98A is shown in FIGS. 2 and 11. FIG. 7 is an exploded view of important portions of laser mounting structure 98 that is supported to one end of cell 10 by means of structural brackets 100 shown in FIGS. 4 and 5. As best seen in FIG. 7 the laser mounting structure 98 includes a support base 102 having integrally formed parallel portions 104 and 106. That is, the support base includes integrally formed portion 104 that is hinged to base 102 about a vertical axis while portion 106 is integrally hinged 15 to portion 104 about a horizontal axis. This unique double axis arrangement permits the alignment of the beam from the laser diode to be very accurately adjusted to provide the critical paths as illustrated in FIG. 9 so that the multiple paths can be accomplished and so the beam properly exits the cell to intersect photo diodes 52 and 64. An alternate embodiment of the double axis beam alignment system of this invention will be described subsequently with reference to FIGS. 2 and 11.

As seen in FIG. 7, an exchanger piece 108 has an integral forwardly extending plug portion 110. Exchanger piece 108 is secured to support base 102 by a spatial ring 112. Positioned on the forward surface of exchanger piece 108 is a non-metallic isolator 114. As will be described in more detail subsequently, mounted on the forward surface 116 of the exchanger piece plug portion 110 is a peltier device 118, a substrate 120, a thermistor 122 and laser diode 14. The structure relationships between metallic drain 110, peltier 118, substrate 120, thermistor 122 and diode 14 are diagrammatically illustrated in FIG. 8.

Figure 8:
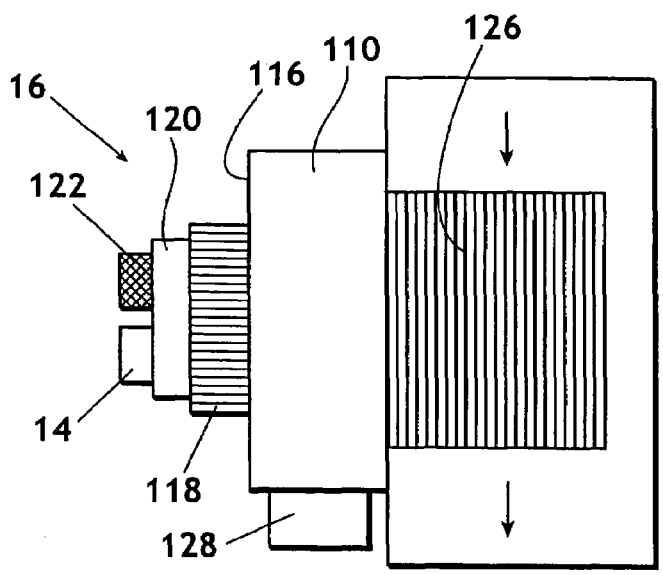
FIG. 8 is a diagrammatic view of the relationship between a laser diode and associated elements by which the temperature of the diode is controlled.

As shown in FIG. 7, the rearward end of exchange piece 108 includes an integral tubular portion 124 that contains therein heat exchange fins 126 (See FIGS. 7 and 8). In a heat conductive relationship with plug portion 110, which functions as a metallic heat drain, is a resister 128 as shown in FIG. 8.

Figure 10:
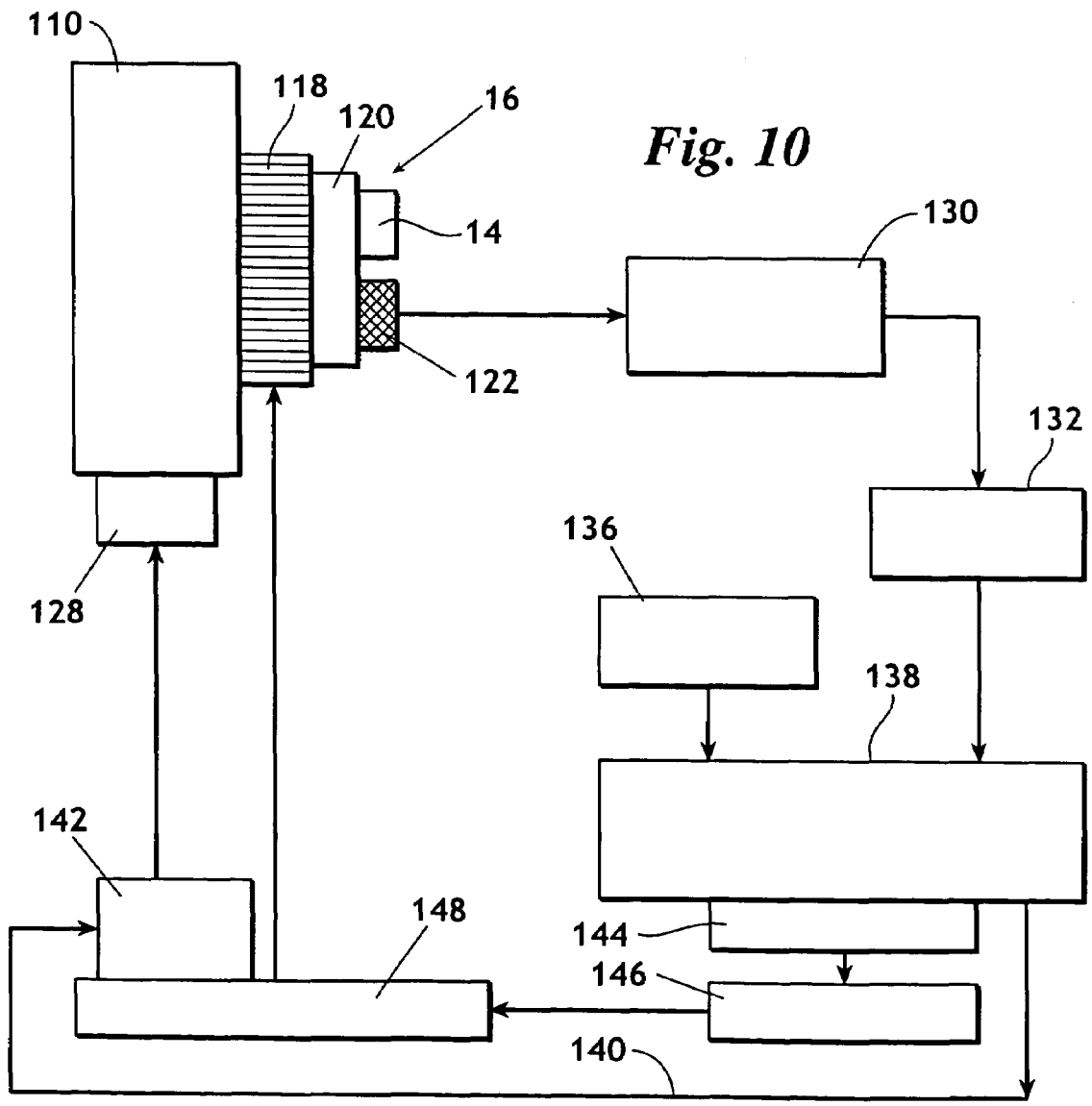
FIG. 10 is a block diagram of the components employed to control the temperature of the light source employed with the Herriott type cell to provide improved accuracy of the system for detecting a selected gas.

An important aspect of the invention is the method and system for controlling the temperature of laser diode 14. For effective measurement of gas concentration by spectrographic absorption of a light beam it is important that the frequency of the light beam be controlled within a narrow range. A laser diode can be designed to provide the frequency of light that is most readily absorbed by methane molecules. However, if the frequency varies from the critical absorption frequency the accuracy of the system is reduced. Further, the frequency of light emitted by a laser diode is affected by the temperature of the diode. The system of this invention for controlling the temperature of laser diode 14 is best illustrated in FIGS. 8 and 10. FIG. 10 diagrammatically shows the relationship between laser diode 14 and its heat control components. Laser diode 14 is secured to a substrate 120 such as by the application of thermo-transmitting adhesive. Also secured to substrate 120 is a thermistor 122. Substrate 120 is bonded to a peltier element 118 that functions as a thermoelectric cooling element. Peltier 118 is thermally bonded such as by soldering, to a metallic drain 110 that is the plug portion of exchanger piece 108 as seen in FIG. 7. The metallic drain in turn is in thermal contact with one or more heat exchanger fins 126 as seen in FIGS. 2, 7 and 8. Also, in thermal contact with metallic drain 110 is a resistor 128 as seen in FIG. 8 and in the electrical diagram of FIG. 10.

Referring to FIG. 10 the electrical interrelationships of the heat control components are illustrated. Thermistor 122 provides a voltage signal proportional to the temperature of substrate 120, which in turn is linked to the temperature of laser diode 14. A signal from thermistor 122 is fed to current generator circuit 130 and the signal from generator 130 is fed to an analog to digital converter 132, the output of which is passed to a microprocessor 138. A temperature selector circuit 136 provides a voltage output directly related to the desired temperature of the substrate 120 and therefore of laser diode 14, the output of which is fed to a microprocessor 138. In microprocessor 138 the signal from the temperature selector circuit 136 is compared with the digitally encoded temperature detected by thermistor 122 to provide an output control signal on conductor 140. The signal on conductor 140 is fed to a heat mode on/off switch 142. When switch 142 is "on" this signal is fed to resistor 128 whose function is to supply heat as required to the heat exchanger plug portion 110.

The output from microprocessor 138 is fed to a peltier control signal generator 144 that in turn is fed to a digital to analog converter 146, the output of which is fed to a peltier current generator 148 which in turn supplies a control current to peltier element 118.

Under most operating conditions the function of the heat exchanger system of the invention is to cool laser diode 14. That is, laser diodes typically generate significant heat and therefore normally it is necessary to remove heat from the laser diode to keep it within the desired operating range. For this reason under normal operating conditions resistor 128 is not employed since its only function is to supply heat when necessary to the plug portion heat exchanger 110 so that by means of peltier 118 the heat is transferred to substrate 120 and thereby functions to provide a warm environment for laser diode 14.

Since it is normally necessary, under typical ambient temperatures to cool the laser, an important aspect of this invention is the concept of utilizing the test gas as a cooling medium. As shown in FIG. 1 the test gas, after having passed through cell 10 is conducted to thermo regulating system 16 that is illustrated in FIGS. 8 and 10 and the elements of which are also illustrated in FIG. 7. Test gas that is moved through cell 10 in which the concentration of methane is determined, also advantageously is used as a cooling medium. The test gas passes out of cell 10 through the cooling system and past cooling fins 126 contained within housing tubular portion 124 as illustrated in FIG. 7 and diagrammatically in FIG. 8.

The current consumed by a laser diode at selected voltages can be used as an indicator of the diode's temperature. That is, as the temperature of a laser diode increases the resistance to current flow increases. This characteristic can be used as a means of regulating the diode's temperature. By noting the current consumed by a diode the temperature control system disclosed in FIGS. 8 and 10 can be employed. Thus, in place of thermistor 122 an ammeter in series with laser diode 14 can be used to supply a control signal to measurement current generator 130 to produce an appropriate signal that is fed to A/D converter 132 and thence to microprocessor 138. By use of proper software the microprocessor directs temperature corrective action by peltier device 118 or resistor 128. While this system has good theoretical possibilities, as a practical matter, achieving the required accuracy of diode temperature control using diode voltage and current has been difficult.

The route taken by sample gas entering and exiting cell 10 is illustrated best by reference to FIG. 3 in conjunction with FIG. 1. After sample gas is drawn into inlet tube 20 and through filter 22, the gas enters cell 10 through a passageway 150 shown in dotted outline in cap member 94. From passage 150, gas enters into an axial recess 152 in the second end 77 of central axle 74. A plurality of spaced apart small diameter passageways 154 extend in radial planes from axial recess 152 to the surface 78 of axle 74 to connect with annular absorption area 84. The plurality of openings 154 serve to equally distribute the sample gas entry into one end of absorption area 84.

The gas traverses within absorption area 84 from the second end 77 to the first end 76 of axle 74. Adjacent the first end 76 of axle 74 are a plurality of passageways 156 in radial planes that communicate with an axial recess 158.

Figure 5:
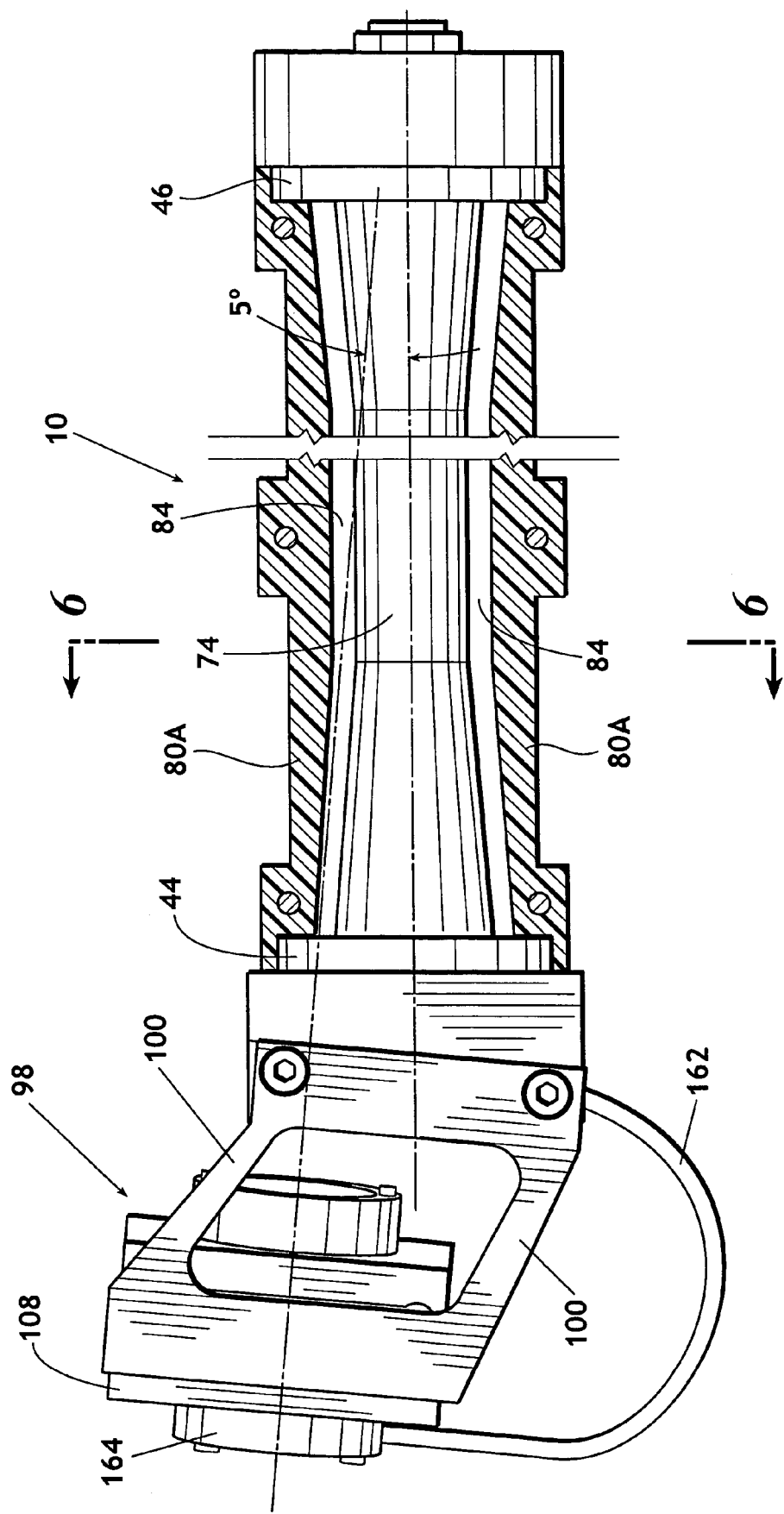
FIG. 5 is a side view taken along the line 5-5 of FIG. 4 showing the gas-detecting cell rotated about its axis by 90° with respect to the view of FIG. 4.
Figure 6:
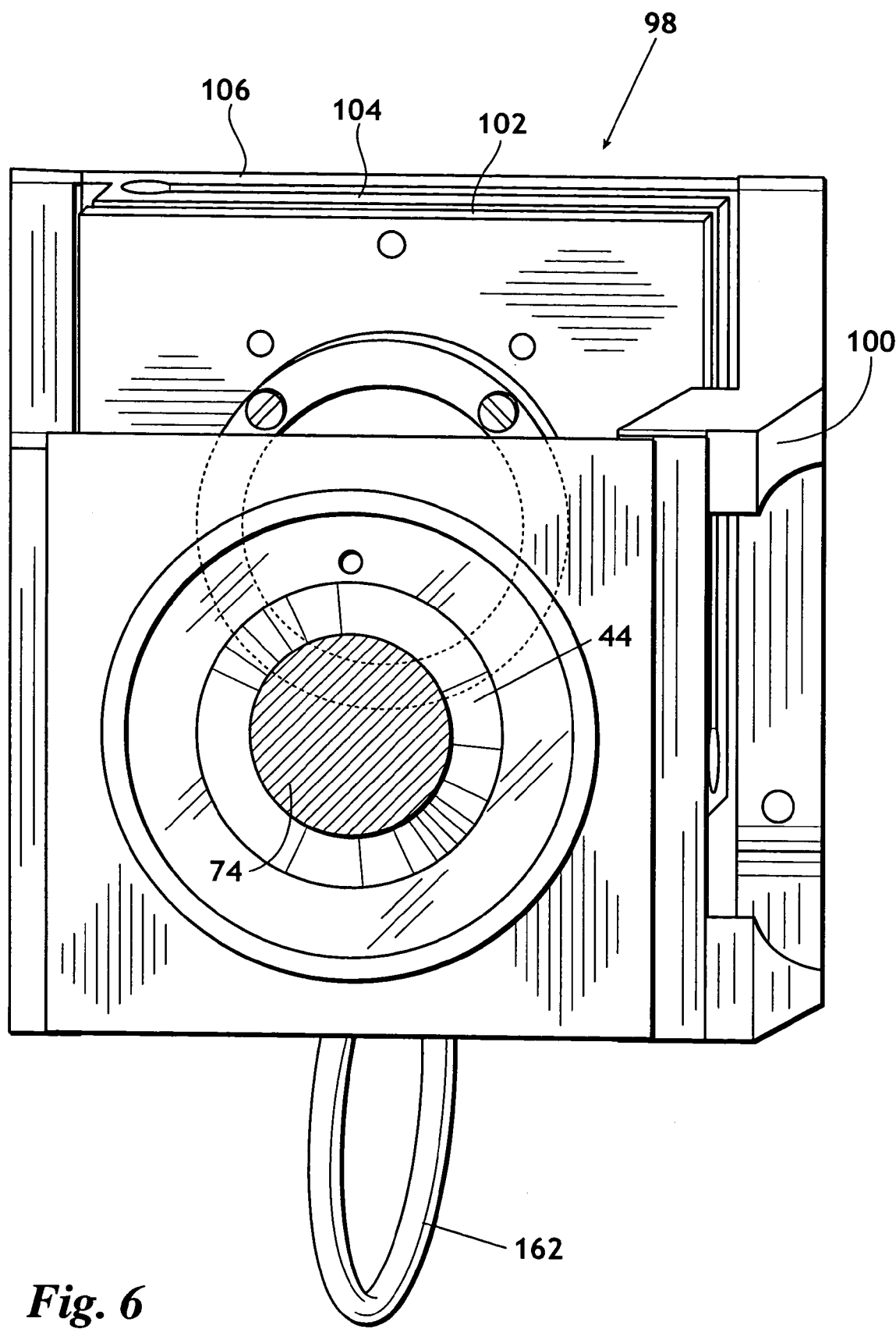
FIG. 6 is a cross sectional view taken along the line 6-6 of FIG. 5. In this Figure the housing sleeves that are revealed in FIGS. 4 and 5 are not shown.

Communicating with axial recess 158 is an exit passageway 160 by which sample gas flows from cell 10. The plurality of small passageways 156 that connect axial recess 158 to annular absorption area 84 are seen in FIGS. 2 and 3. Sample gas after passing out of cell 10 through exit passageway 160 flows through a length of flexible tubing 162 (see FIG. 5). Closing the rearward end of exchanger piece 108 is an end cap 164 that has a radial passageway 166 that receives an end of flexible tube 162 as shown in FIG. 5. A second passageway 168 in cap 164 (see FIG. 7) provides for communication with gas pump 26 as seen in FIG. 1 which can be accomplished such as by a flexible tube 170 illustrated in FIG. 1, but not shown on the other figures. Sample gas is drawn by the action of pump 26 to move into annular absorption area 84 in a way that the gas is equally distributed around the entire annular passageway so that as a light beam is bounced repeatedly between opposed mirrors 44 and 46, the opportunity for absorption of the light beam is equally distributed and in an arrangement wherein gas passageways are most effectively formed within the end portions of axle 74.

The cell for measuring the concentration of a preselected gas, such as methane as illustrated and described herein is generally configured to operate at or near atmospheric pressures however the system functions successfully in the range of about 0.1 to about 2.0 atmospheres. Basically, the system as illustrated is not intended to test high-pressure gas samples.

The gas detecting system of this invention is particularly adaptable for use in conducting a survey of a geographical area to find where gas leakage may be occurring. The gas detection system herein is particularly adapted for use as a survey instrument due to the confined annular absorption area that is achieved by the use of a center axle 74 surrounded by housing components 80A and 80B resulting in a relatively small volume sample gas test area having a relatively long path for a light beam to pass. Sample gas within the test area is quickly changed by the continuous action of gas pump 26. Taking advantage of these unique features adapts the gas detection system of this invention to be moved at a relatively fast rate (compared to existing gas detection systems) over a geographical area. Specifically, the gas detection instrument as described herein can be moved about by a moving vehicle at a speed that enables a relatively large geographical area to be checked for possible gas leakage in a relatively short time.

When the system of this invention is transported by a vehicle it is important that the sample gas inlet 18 as seen in FIG. 1 be extended exteriorly of the vehicle so that gas is constantly drawn into the system from the local environment as the vehicle moved from one part of a geographical area to another.

In order to provide accurate information as to areas of gas concentration that may be significant, the system of this invention is particularly adaptable for use with a global positioning system 172 as indicated in FIG. 1. Global positioning system 172 is in communication with microprocessor 42. Further, by use of a printer 174 coupled to microprocessor 42 and global positioning system 172, a map can be generated with a printout of detected gas concentration levels. A user can survey an area, such as a plant site, a village, an industrial park, a portion of a larger city, or any area of interest, and obtain a map with indicated levels concentration of a specific gas, such as methane. In this way, a user can quickly determine the areas where increased gas concentration exists and the instrument of this invention can then be returned to that area where it can be carried about (as opposed to being transported in a vehicle) for more detailed inspection to determine where gas leaks are occurring.

FIGS. 2 and 11 show an alternate embodiment of a laser mount structure 98A that has a different double axis arrangement for alignment of the beam from the laser diode. A structural bracket 176 is secured to the forward end of cell 10. Bracket 176 supports a base plate 178 (see FIG. 11). An adjustable plate 180 is hinged to base plate 178 by a thin, flexible, first hinge sheet 182. A second thin, flexible, hinge sheet 184 (see FIGS. 2 and 11) supports exchange piece 186 having a tubular portion 188 that functions as a heat exchange housing, the outer end of which is closed by an end cover 190. Tubular portion 188 houses heat exchange fins 126. Tubular portion 188 has passageways 166A and 168A for the flow of sample gas corresponding to passageways 166 and 168 as described with reference to FIG. 7.

The hinge sheets 182 and 184 bend within their elastic limits as the laser beam is aligned with cell 10 and therefore serve the same function as the integrally formed hinges of parallel portions 104 and 106 of support plate 102 as described with reference to FIG. 7. Both structures permit the laser diode to pivot about axii that are in perpendicular planes. The laser mount structure 98A of FIGS. 2 and 11 is preferred to the laser mount structure of FIG. 7 due to its economy of manufacture. Otherwise, the two embodiments function the same way to do the same thing and achieve the same results.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claims, including the full range of equivalency to which each element thereof is entitled.

What is claimed is:

1. A method of measuring the concentration level of a preselected gas in an environment, comprising:
   (1) continuously moving a stream of sample gas from the environment through a confined testing area within a detecting instrument;
   (2) energizing a light source to emit a light beam of a frequency that is highly absorbed by the preselected gas;
   (3) splitting said light beam into three components;
   (4) passing a first component of said light beam to a first photo detector for providing a first electrical signal indicative of the intensity of said light beam;
   (5) passing a second component of said light beam multiple times through said confined testing area and thence to a second photo detector for providing a second electrical signal indicative of a concentration measurement corresponding to a lower concentration level;
   (6) passing a third component of said light beam over a reduced length path through said confined testing area and thence to a third photo detector for providing a third electrical signal indicative of a concentration measurement corresponding to a higher concentration level; and
   (7) employing said first, second, and third electrical signals for determining the concentration level of said preselected gas in said stream of sample gas.

2. A method according to claim 1 wherein said preselected gas is selected from the group comprising methane, butane, propane, ethane, oxygen, hydrogen, nitrogen, $H_2O$, hydrogen fluoride, hydrogen chloride, hydrogen boride, hydrogen sulfide, ammonia, CO, $CO_2$, NO, $NO_2$ and $SF_6$.

3. A method according to claim 1 wherein said light source is a laser diode.

4. A method according to claim 1 wherein said light source is a light emitting diode.

5. A method according to claim 1 including a heat control assembly that includes a heat sink in thermal communication with said light source, said heat sink including a heat dissipater past which said stream of sample gas flows.

6. A method according to claim 1 wherein said detecting instrument is in the form of a Herriot-type multipass cell.

7. A cell for use in measuring the concentration of a preselected gas in a gas sample, comprising:
   an axle having a forward and a rearward end;
   a housing surrounding and spaced from an external surface of said axle providing an annular absorption area;
   a pump for moving the gas sample through said absorption area;
   a first annular mirror supported at said axle forward end and having an entry aperture therein;
   a second annular mirror supported at said axle rearward end and having an exit aperture therein;
   a light source supported forwardly of said first mirror that, when energized, generates a light beam passing through said entry aperture and into said annular absorption area to be reflected repeatedly between said mirrors, the light beam after multiple reflections passing out through said exit aperture;
   a first photo detector for indicating the intensity of said light beam entering said entry aperture;
   a second photo detector rearwardly of said second mirror in alignment with said exit aperture to receive the impingement of said light beam;
   a third photo detector positioned outwardly of said second annular mirror to receive a portion of said light beam that passes through said second annular mirror after said light beam has traveled a reduced length path through said annular absorption area whereby a concentration measurement corresponding to a higher concentration level can be measured; and
   instrumentation connected to said first, second and third photo detectors by which the absorption of said beam is measured and by which the concentration of the preselected gas in the gas sample can be determined.

8. A cell for use in measuring the concentration of a preselected gas in a gas sample according to claim 7 including:
   a window between said light source and said entry aperture that is positioned at an angle of incidence to said light beam, a portion of said light beam being reflected by the window to strike said first photo detector.

9. A cell for use in measuring the concentration of a preselected gas in a gas sample according to claim 7 including passageways in said axle communicating said forward and rearward ends with said absorption area surrounding said axle by which sample gas flows into, through and then out of said absorption area.

10. A cell for use in measuring the concentration of a preselected gas in a gas sample according to claim 7 wherein said housing is formed of a first and a second half shell that is positioned around said axle and that is configured to define said annular absorption area.

11. A cell for use in measuring the concentration of a preselected gas in a gas sample according to claim 9 including a thermoelectric cooler thermally coupled to said light source and control circuitry whereby the temperature of said light source is controlled.

12. A cell for use in measuring the concentration of a preselected gas in a gas sample according to claim 11 including a substrate on which said light source is mounted and including a thermistor mounted on said substrate providing a measurement of the temperature of said substrate and thereby said light source, the thermistor coupled to said control circuitry.

13. A cell for use in measuring the concentration of a preselected gas in a gas sample according to claim 7 wherein said light source is a laser-emitting diode.

14. A cell for use in measuring the concentration of a preselected gas in a gas sample according to claim 7 wherein said light source is a light-emitting diode.

15. A cell for use in measuring the concentration of a preselected gas in a gas sample according to claim 11 wherein said light source and said thermoelectric cooler are mounted in a chamber supported to said cell and including a heat exchanger and wherein said chamber is thermally isolated from said heat exchanger.

16. A cell for use in measuring the concentration of a preselected gas in a gas sample according to claim 7 including a pump connected to draw sample gas into and through said annular absorption area by means of piping and including a filter system in series with said annular absorption area and pump, wherein said pump, piping and filter systems are specified and sized so that the pressure of sample gas within said absorption area is between about 0.1 to 2.0 atmospheres.

17. A cell for use in measuring the concentration of a preselected gas in a gas sample according to claim 7 including a heat exchange system thermally coupled to said light source, a pump for moving sample gas through said absorption area and including piping for moving the sample gas past the heat exchanger system.

18. A cell for use in measuring the concentration of a preselected gas in a gas sample according to claim 7 including:
    a global positioning system providing a signal identifying the geographical location of the cell; and
    a display connected to instrumentation and to said global positioning system providing a display of detected gas concentrations at different geographical locations.

19. A cell for use in measuring the concentration of a preselected gas in a gas sample according to claim 7 wherein said light source is contained in a light mounting structure that is supported to the cell forwardly of said first mirror and wherein said light mounting structure is pivotal about two divergent axii that are in perpendicular planes permitting accurate alignment of said light beam with said entry aperture and said annular mirrors.

20. A cell for use in measuring the concentration of a preselected gas in a gas sample according to claim 19 wherein first and second planar sheets form hinges in diametric planes providing said two divergent axii of pivotation.

21. A cell for use in measuring the concentration of a preselected gas in a gas sample according to claim 13 wherein said laser-emitting diode is energized by a pulsed current having a generally saw tooth pattern whereby the frequency of light emitted by each voltage pulse covers a selected band.

22. A cell for use in measuring the concentration of a preselected gas in a gas sample according to claim 7 wherein the cell is transported in a vehicle and wherein the gas sample is continuously replaced while the vehicle is in motion by withdrawing sample gas from exterior of the vehicle.

* * * * *